(12) United States Patent
Cerami et al.

(10) Patent No.: US 6,174,526 B1
(45) Date of Patent: Jan. 16, 2001

(54) BLOOD-BORNE MESENCHYMAL CELLS

(75) Inventors: Anthony Cerami, Shelter Island; Richard J. Bucala, New York, both of NY (US)

(73) Assignee: The Picower Institute for Medical Research, Manhaset, NY (US)

( * ) Notice: Under 35 U.S.C. 154(b), the term of this patent shall be extended for 0 days.

(21) Appl. No.: 08/487,116

(22) Filed: Jun. 7, 1995

Related U.S. Application Data

(63) Continuation of application No. 08/023,290, filed on Feb. 26, 1993, now Pat. No. 5,654,186.

(51) Int. Cl.$^7$ .............................. A01N 65/00; C12N 5/08
(52) U.S. Cl. ..................... 424/93.1; 424/93.7; 435/372; 435/375
(58) Field of Search .................................. 435/372, 375; 424/93.1, 93.21, 93.7, 529, 577

(56) References Cited

U.S. PATENT DOCUMENTS 5,197,985 * 3/1993 Caplan et al. .
5,226,914 * 7/1993 Caplan et al. .

FOREIGN PATENT DOCUMENTS

WO 92/22584   12/1992 (WO) .

OTHER PUBLICATIONS

Certified English translation of Voskresenkii et al. (1988) Ontogenesis (19):247–52.
Caplan, A.I. (1990) Biomat 11:89.
Haynesworth et al. (1992) Bone 13:69–80.
Haynesworth et al. (1992) Bone 13:81–88.
Nakahara et al. (1990) Bone 11:181–8.
Nakahara et al. (1991) Experimental Cell Res. 195:492–503.
Bucala et al. (1993) The FASEB J. 7:A139.
Andreoni et al. (1990) Exp. Hematol. 18:431.
Allgower, M. (1956) In: The Cellular Basis of Wound Repair, Charles C. Thomas Publisher, Springfield, Illinois, USA,. pp. 44–50 and 108.
Allgower, M. (1963) Proceedings of a Workshop, The Committee on T, National Academy of Science—National Research Council, 5–8, Dec., pp. 160–164.
Allgower, M. (1974) Cellular Basis of Wound Repair, International Symposium on Wound Healing, Rotterdam, pp.16–20.

* cited by examiner

*Primary Examiner*—David Saunders
*Assistant Examiner*—Mary Beth Tung
(74) *Attorney, Agent, or Firm*—Davis Wright Tremaine LLP

(57) ABSTRACT

The present invention relates to a population of blood borne mammalian cells that express a unique profile of surface markers that includes certain markers typical of connective tissue fibroblasts, and are referred to herein as "blood-borne mesenchymal cells." In particular, it relates to the isolation, characterization and uses of such blood-borne mesenchymal cells. The cells of the present invention can be distinguished from peripheral blood leukocytes by their distinct size, morphology, cell surface phenotype and biologic activities, and are likewise distinguishable from connective tissue fibroblasts by other surface phenotypic markers. These cells proliferate in culture, and in vivo, as demonstrated in animal models, are capable of migrating into wound sites from the blood. Therefore, such blood-borne mesenchymal cells may have a wide range of applications, including, but not limited to, the promotion of wound healing, tissue remodeling, and for gene therapy.

8 Claims, 2 Drawing Sheets

BLOOD-BORNE MESENCHYMAL CELLS

Figure 1A:
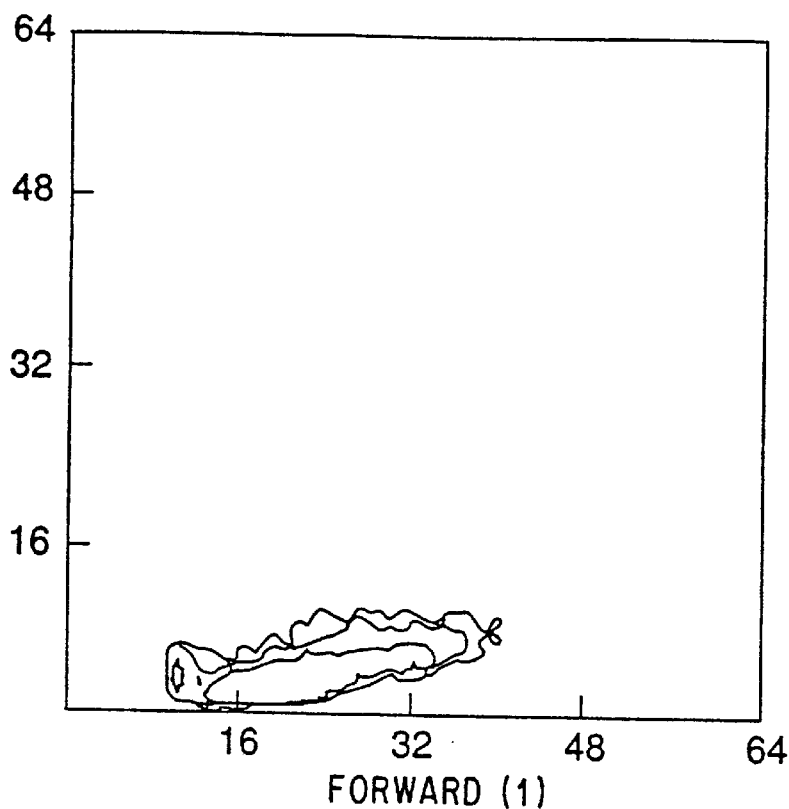

This application is a Continuation of application Ser. No. 08/023,290, filed Feb. 26, 1993 now U.S. Pat. No. 5,654,186.

1. TECHNICAL FIELD OF THE INVENTION

The present invention relates to a population of blood-borne mammalian cells that express a unique profile of surface markers that includes certain markers typical of connective tissue fibroblasts, and are referred to herein as "blood-borne mesenchymal cells." In particular, it relates to the isolation, characterization and uses of such blood-borne mesenchymal cells. The cells of the present invention can be distinguished from peripheral blood leukocytes by their distinct size, morphology, cell surface phenotype and biologic activities, and are likewise distinguishable from connective tissue fibroblasts by other surface phenotypic markers. These cells proliferate in culture, and in vivo, as demonstrated in animal models, are capable of migrating into wound sites from the blood. Therefore, such blood-borne mesenchymal cells may have a wide range of applications, including, but not limited to, the promotion of wound healing, tissue remodeling, and for gene therapy.

2. BACKGROUND OF THE INVENTION

2.1. WOUND HEALING

A wound can be considered a physical interruption in the normal architecture of tissues, which can result from physical or chemical causes, such as burns, abrasions, cuts and surgical procedures. In the case of skin, since it normally functions as a first line of defense, a cutaneous wound may severely compromise an individual's ability to resist infectious agents, rendering the individual susceptible to opportunistic infections, in addition to pain and discomfort. Therefore, it is highly desirable to develop agents and methods for using them to promote a rapid wound healing response.

Once a wound occurs, the body initiates a coordinated repair response which is a complex process of events involving both humoral and cellular elements, and which occurs over a time period of days to weeks. In particular, it has been shown that wound healing depends on the interactions between specific cell types, cytokines and extracellular matrix (Clark, 1989, Curr. Opinion Cell Biol. 1:1000). A first step in wound healing involves the action of blood-borne cells known as platelets. These cells aggregate at wound sites and form a temporary barrier that prevents blood loss. Platelets achieve this function by secreting thrombin, which catalyzes blood clot formation, and other factors, which serve to attract other cells into the damaged area.

After the first 24 hours, additional cellular elements arrive and contribute to the wound healing process. Blood-borne neutrophils and monocytes migrate into the wound site. These cells function in part by neutralizing invading microorganisms and secreting enzymes that clear away the initial clot. During this second, often referred to as "inflammatory" phase of wound repair, macrophages play a primary role by secreting a variety of inflammatory cytokines such as tumor necrosis factor (TNF), the interleukins such as IL-1, IL-6, IL-8, transforming growth factor-β (TGF-β), etc., and growth factors such as epidermal growth factor (EGF), fibroblast growth factor (FGF) and platelet-derived growth factor (PDGF), that serve to combat infection and recruit additional cell types. These cell types include the epithelial and connective tissue cells particularly fibroblasts, that ultimately repair the site of tissue damage. The final phase of tissue repair is tissue remodeling, involving collagen cross-linking, collagenolysis and collagen synthesis for increasing structural integrity within the wound. Unfortunately, this entire process takes a relatively long time to complete.

Various approaches have been studied in recent years in an attempt to accelerate the wound repair process so as to prevent or minimize infections and further damage to the underlying tissues. A more traditional approach involves the grafting of healthy tissues upon a wound site, particularly the use of autologous tissues obtained from a different part of the body of the same individual (Bell et al. 1983, J. Invest. Dermatol. 81:25). Another approach involves the administration of cytokines known to be capable of promoting chemotaxis and cellular proliferation. Such cytokines include PDGF, TGFβ and FGF (Pierce et al., 1989, J. Cell. Biol. 109:429; Rappolee et al., 1988, Science 241:708).

2.2. CELL TYPES INVOLVED IN WOUND HEALING

Over a period of days to weeks, tissue repair and remodeling processes continue to take place. In skin, epithelialization occurs as neighboring, epithelial cells grow into the wound site to protect it while the subjacent dermis is repaired. Connective tissue mesenchymal cells, also referred to as fibroblasts are the primary mediators of this later phase of wound healing. These cells proliferate within the wound site and produce collagens and other matrix components. During this phase, a cellular and macromolecular framework is established that is responsible for the ultimate reorganization of a particular tissue or organ. Smooth muscle cells and vascular endothelial cells also repopulate the wound site. New blood vessels form to support and nourish the newly established tissue.

The major cellular mediators of wound repair include blood-borne platelets and leukocytes such as neutrophils and monocytes which become macrophages as they migrate into the wound area. These blood-derived leukocytes combat infection, and secrete cytokines and growth factors. In addition, fibroblasts in the surrounding connective tissues also grow into the site of injury to provide additional cytokines and extracellular matrix proteins. However, prior to the present invention, a blood-borne population of fibroblast-like cells that possesses the capability of participating in and enhancing wound healing processes had never been described.

3. SUMMARY OF THE INVENTION

The present invention relates to mammalian blood-borne mesenchymal cells involved in wound healing, methods of isolating the cells, and methods of using the cells in promoting wound healing processes and tissue remodeling.

The invention is based, in part, on the Applicants' discovery that a distinct population of relatively large, spindle-shaped, fibroblast-like cells can be isolated and cultured from the human and murine peripheral blood. Phenotypic analysis of these cells with antibodies specific for various known cell markers reveals that they are of mesenchymal origin, as they express typical fibroblast markers such as collagen, vimentin and fibronectin. In cell culture, the large spindle-shaped cells co-exist with small round cells that also display a fibroblast-like phenotype. Thus, these mesenchymal cells are distinguishable from peripheral blood leukocytes by their cell size, morphology and unique phenotype.

Because of the correspondence of this profile of surface markers to fibroblasts rather than known blood cell types, these cells are referred to herein as "blood-borne mesenchymal cells." The invention is described by way of examples in which human blood-borne mesenchymal cells are isolated, cultured and their cell surface phenotype characterized. In vitro, the cultured mesenchymal cells expand in numbers in response to granulocyte-macrophage colony stimulating factor (GM-CSF) in a dose-dependent manner. In vivo, a corresponding murine cell population is observed to migrate into wound chambers that have been experimentally-implanted into animals.

A wide variety of uses of the blood-borne mesenchymal cells, and factors produced by these cells, are encompassed by the invention described herein, particularly to improve wound healing, including, but not limited to, cutaneous wounds, corneal wounds, wounds of epithelial-lined organs, resulting from physical abrasions, cuts, burns, chronic ulcers, inflammatory conditions and the like, as well as from any surgical procedure. Alternatively, the mesenchymal cells may be genetically engineered to express one or more desired gene products. The engineered cells may then be administered in vivo (e.g., either returned to the autologous host or administered to an appropriate recipient) to deliver their gene products locally or systemically.

4. BRIEF DESCRIPTION OF THE DRAWINGS

FIG. 1. Forward and side scattering of incident light during cytofluorography demonstrating the increase in size and granularity of cell populations after time in culture.

FIG. 1A. Freshly isolated peripheral blood lymphocytes before culture.

Figure 1B:
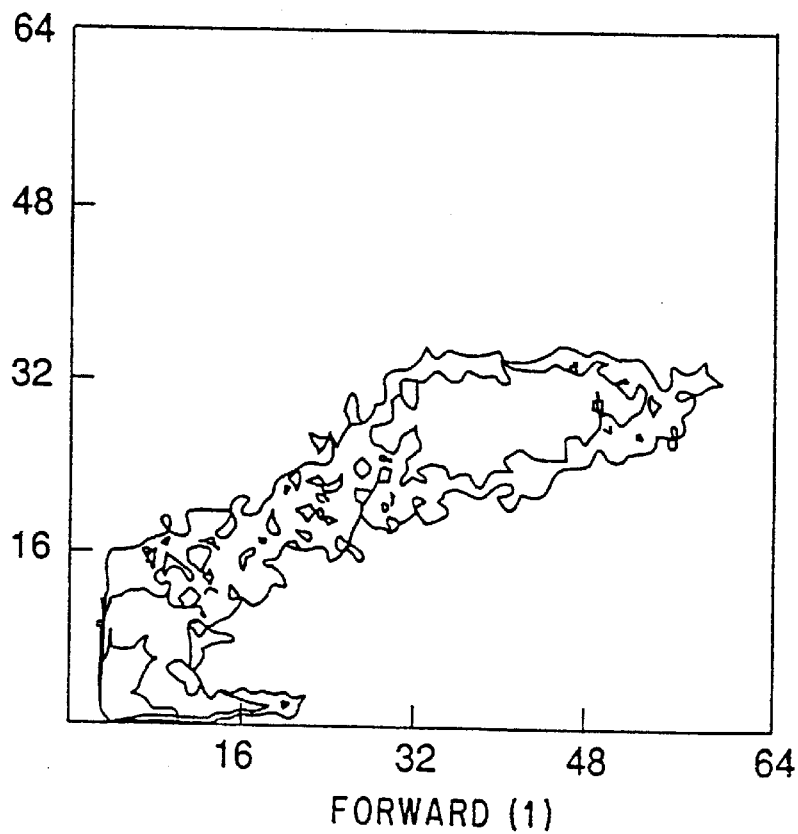

FIG. 1B. Cells recovered after 4 weeks in culture.

Figure 2:
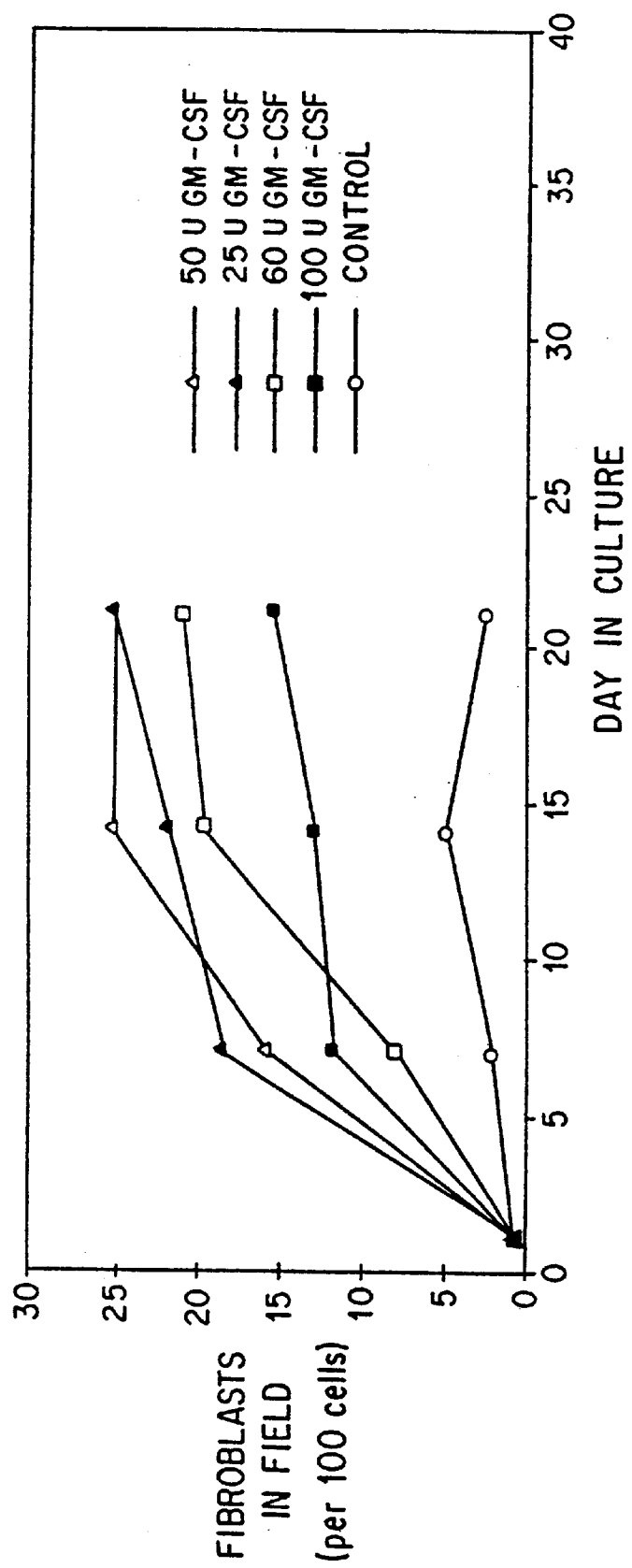

FIG. 2. Proliferation of blood-borne mesenchymal cells in response to granulocyte macrophage-colony stimulating factor.

5. DETAILED DESCRIPTION OF THE INVENTION

The present invention relates to mammalian blood-borne mesenchymal cells, to methods of isolating and characterizing the cells, and to methods of using the same for a variety of applications including but not limited to wound healing and gene therapy.

The invention is discussed in more detail in the subsections below, for purposes of description and not by way of limitation. The specific procedures and methods described and exemplified for the isolation of the mesenchymal cells from human blood are merely illustrative. Analogous procedures and techniques known in the art are equally applicable. In addition, similar techniques may be applied for the isolation of mesenchymal cells from the blood of non-human mammals.

5.1. ISOLATION OF THE BLOOD-BORNE MESENCHYMAL CELLS

The present invention provides for methods of enriching and/or purifying mesenchymal cells from peripheral blood or other physiological sources of these cells. The biologic activity of these cells may allow for their uses in settings where absolute purity is not achieved. Although the blood is preferred, the mesenchymal cells of the invention may be isolated from any tissue where they reside or from which they may mature, including but not limited to the bone marrow, fetal liver, or embryonic yolk sac.

A variety of separation procedures may be employed for obtaining mesenchymal cells involved in wound healing from the peripheral blood. Variants of such methods which are illustrated in the working examples described in Section 6 are included within the scope of the present invention. In accordance with this aspect of the invention, blood-borne mesenchymal cells may be isolated by separation based on the presence or absence of specific cell surface markers. These techniques may include flow cytometry using a fluorescence activated cell sorter or biotin-avidin or biotin-streptavidin separations using biotin-conjugated to marker-specific polyclonal or monoclonal antibodies and avidin or streptavidin bound to a solid support such as affinity column matrix or plastic surfaces, magnetic separations using antibody-coated magnetic beads, destructive separations such as antibody plus complement or antibody coupled to cytotoxins or radioactive isotopes for the removal of undesirable cell populations.

Alternatively, such mesenchymal cells may be isolated by procedures involving repetitive density gradient centrifugation, lectin chromatography, affinity chromatography involving positive selection and negative selection, or a combination thereof. Positive selection methods may utilize affinity chromatography with antibodies directed to mesenchymal cell-specific surface markers. For example, most mononuclear cells may be depleted first from the blood after density gradient centrifugation and plastic adhesion, then an antibody to vimentin antigen can be used to positively select for mesenchymal cells. Negative selection includes modifications of the protocol disclosed herein, infra. In essence, a mesenchymal cell preparation may be reacted with one or more antibodies directed at cell surface antigens not expressed by mesenchymal cells for their removal. Antibodies to any T cell, B cell, monocyte, natural killer (NK) cell, dendritic cell and granulocyte markers may be used. Examples of such antibodies include anti-CD3, anti-CD4, anti-CD5, anti-CD8, anti-$\alpha\beta$ and anti-$\gamma\delta$ T cell receptor specific for T cells; anti-CD12, anti-CD19 and anti-CD20 specific for B cells; anti-CD14 specific for monocytes; and anti-CD16, and anti-CD56 specific for NK cells. These antibodies may be applied in any combination repeatedly or in a sequential manner for the enrichment of mesenchymal cells. Upon binding to the antibodies, the cells may be removed by adsorption to a solid surface coated with an anti-mouse antibody column, as the majority of monoclonal antibodies directed at cell surface markers are of mouse origin, or if the antibodies are conjugated with biotin, the antibody-bound cells can be removed by an avidin-coated surface; or if the antibodies are conjugated to magnetic beads, the cells expressing antigens recognized by the antibodies can be removed in a magnetic field.

5.2. CHARACTERIZATION OF THE BLOOD-BORNE MESENCHYMAL CELLS

As shown by the examples described herein, blood-borne cells are detectable immunochemically in the peripheral blood, and may be purified to homogeneity by various procedures. The cells in short-term cultures fall into two distinct morphological profiles, a "round" cell type and "spindle-shaped" fibroblast-like cell type. In these short term cultures, the round cells appear to be a mixture of lymphocytes and a small round cell type which, like the spindle-shaped cells, demonstrate a fibroblast-like phenotype. Long-term culture appears to enhance the growth of the mesenchymal cells, i.e., both the round and spindle-shaped cells which display the fibroblast-like phenotype, until they become the dominant cell type in vitro. The small round mesenchymal cells may represent the mitotically active stage of the spindle-shaped mesenchymal cells. Thus, it appears that the initial population of lymphocytes present in the short-term cultures, i.e., cells which are known to have a finite life-span in culture in the absence of specific lymphokines, eventually yield to the more persistent mesenchymal cells.

The cells of the present invention are characterized to be of mesenchymal origin primarily because of their unusual cell surface phenotype for blood-derived cells. In particular, these cells express vimentin, fibronectin, collagen I and III, which are typical markers for fibroblasts. Conversely, these cells do not express cytokeratin, von Willebrand's factor, desmin, laminin and smooth muscle cell α-actin, all of which are commonly used markers for epithelial, endothelial or smooth muscle cells. Further, the antigens that are typically expressed on peripheral blood leukocytes such as CD3, CD4, CD8, and CD56 are also not present on the blood-borne mesenchymal cells. Interestingly, these cells are positive for CD34, which is a marker on hematopoietic stem cells, suggesting that the mesenchymal cells described herein may be bone marrow-derived.

The mesenchymal cells of the present invention are larger and more granular than peripheral blood leukocytes when assessed by forward and side scattering of incident light during cytofluorography. They exhibit a unique spindle-shaped morphology which is typical for fibroblasts, but atypical for other blood-derived cells. Hence, taken collectively, the blood-borne mesenchymal cells appear to be a distinct cell type which is different from all previously described cell populations from the blood, based on their cell size, cell surface phenotype, and morphological properties.

5.3. CULTURING AND EXPANSION OF BLOOD-BORNE MESENCHYMAL CELLS

Isolated blood-borne mesenchymal cells proliferate in vitro in culture media for extended periods of time using standard culture techniques that are well known to those skilled in the art. Preferably, serum-enriched medium should be used, and more preferably medium containing 20% fetal bovine serum should be used, e.g. see Section 6.1.1, infra. It has been shown that their growth may be further enhanced by the addition of GM-CSF. As explained supra, short term cultures derived from peripheral blood lymphocytes contain a contaminating population of lymphocytes, whereas cells positive for fibroblast markers predominate in the long term cultures. GM-CSF accelerates the time course over which the fibroblast-like cells dominate the culture. Alternatively, isolated cells may be engineered to express endogenous GM-CSF to sustain their long-term growth in an autocrine fashion (See Section 5.4, infra). Continuous cell lines or clones generated in this manner may facilitate further isolation of cell surface markers and cytokines and the genes encoding therefor. Long-term culture of blood-borne mesenchymal cells may be performed in tissue culture flasks, roller bottles, bioreactor systems and any culture methods known in the art. In fact, these mesenchymal cells may respond to a number of other conventional cytokines and growth factors.

5.4. USES OF BLOOD-BORNE MESENCHYMAL CELLS

The ability of the blood-borne mesenchymal cells to proliferate in culture indicates that they may be expanded in numbers for use in wound healing, or gene therapy applications, particularly in autologous and syngeneic hosts. To that end, the cells may be used directly after isolation, or after in vitro culture with or without the introduction of exogenous genes, and with or without expression in culture.

A major impediment in the current attempts to achieve stable integration of foreign genes in eukaryotic host cells of different organs is the inability of most of these cells to proliferate in vitro. Since the mesenchymal cells proliferate in vitro, especially in response to GM-CSF, these cells may be ideal candidates as recipients for the introduction of exogenous genes in culture. In addition to the cytokines normally synthesized by the blood-borne mesenchymal cells, a number of other cytokine or adhesion molecule genes may be engineered into these cells to further augment their ability to promote and accelerate wound healing and tissue remodeling, or to deliver products of any gene introduced into the mesenchymal cell for therapeutic purposes.

In general, genetic engineering of the cells involves isolating blood-borne mesenchymal cells from an individual, transferring a gene of interest into these cells, confirming stable integration and expression of the desired gene products. Such genetically engineered cells may be transplanted into the same, or an HLA-matched, or otherwise suitable patient and/or used as a source of factors and/or genes encoding factors made by the cells. For the practice of the invention, mesenchymal cells isolated by the procedures described in Section 6, infra, may be used as recipients in gene transfer experiments. The cells may be grown in culture prior to, during, and after introduction of an exogenous gene. The proliferative activity of these cells may be enhanced by GM-CSF. For the introduction of exogenous genes into the cultured mesenchymal cells, any cloned gene may be transferred using conventional techniques, including, but not limited to, microinjection, transfection and transduction.

One method of gene transfer utilizes recombinant viruses, such as retroviruses or adenoviruses. For example, when using adenovirus expression vectors, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a nonessential region of the viral genome (e.g., region E1 or E3) will result in a recombinant virus that is viable and capable of expressing the gene product in infected mesenchymal cells (e.g., see Logan & Shenk, 1984, Proc. Natl. Acad. Sci. USA 81: 3655–3659). Alternatively, the vaccinia virus 7.5K promoter may be used. (e.g., see, Mackett et al., 1982, Proc. Natl. Acad. Sci. USA 79: 7415–7419; Mackett et al., 1984, J. Virol. 49: 857–864; Panicali et al., 1982, Proc. Natl. Acad. Sci. USA 79: 4927–4931). Vectors based on bovine papilloma virus which have the ability to replicate as extrachromosomal elements are also candidates (Sarver, et al., 1981, Mol. Cell. Biol. 1: 486). Shortly after entry of this DNA into cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, a retroviral genome can be modified for use as a vector capable of introducing and directing the expression of any gene of interest in the blood-borne mesenchymal cells (Cone & Mulligan, 1984, Proc. Natl. Acad. Sci. USA 81:6349–6353). High level expression may also be achieved using inducible promoters, including, but not limited to, the metallothionine IIA promoter and heat shock promoters.

For long-term, high-yield production of recombinant proteins, stable expression is often preferred. Rather than using expression vectors which contain viral origins of replication, the mesenchymal cells can be transformed with a cDNA controlled by appropriate expression control elements (e.g., promoter, enhancer, sequences, transcription terminators, polyadenylation sites, etc.), and a selectable marker. The selectable marker confers resistance to the selection and allows cells to stably integrate the recombinant DNA into their chromosomes and grow to form foci which in turn can be cloned and expanded into cell lines. For example, following the introduction of foreign DNA, engineered mesenchymal cells may be allowed to grow for 1–2 days in an enriched media, and then are switched to a selective media. A number of selection systems may be used, including but not limited to the herpes simplex virus thymidine kinase (Wigler, et al., 1977, Cell 11: 223), hypoxanthine-guanine phosphoribosyltransferase (Szybalska & Szybalski, 1962, Proc. Natl. Acad. Sci. USA 48: 2026), and adenine phosphoribosyltransferase (Lowy, et al., 1980, Cell 22: 817) genes. Also, antimetabolite resistance can be used as the basis of selection for dhfr, which confers resistance to methotrexate (Wigler, et al., 1980, Proc. Natl. Acad. Sci. USA 77: 3567; O'Hare, et al., 1981, Proc. Natl. Acad. Sci. USA 78: 1527); gpt, which confers resistance to mycophenolic acid (Mulligan & Berg, 1981, Proc. Natl. Acad. Sci. USA 78: 2072); neo, which confers resistance to the aminoglycoside G-418 (Colberre-Garapin, et al., 1981, J. Mol. Biol. 150: 1); and hygro, which confers resistance to hygromycin (Santerre, et al., 1984, Gene 30: 147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85: 8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Blood-borne mesenchymal cells may be isolated from the peripheral blood and expanded in culture for a variety of therapeutic purposes, including but not limited to the enhancement of wound healing. Isolated blood-borne mesenchymal cells which are purified or partially enriched with or without exogenous genes may be directly applied to external wound sites including, but not limited to, severe wounds, burns, cuts, abrasions, chronic ulcers and inflammatory diseases of skin. Cosmetic applications of these cells are also within the scope of this invention.

Furthermore, the cells may be directly applied to damaged tissues or organs such as those resulting from trauma or in the course of surgery, for the repair of internal organs, e.g., gastric mucosa, cardiac tissue, bone, and vascular tissue, as well as tissues that are difficult to heal by traditional methods, e.g., joint cartilage, ligaments, tendons, and neural tissue.

Alternatively, the cells may be administered to patients via any of a number of routes, including but not limited to intravenous, intramuscular, subcutaneous, intradermal, etc., for the treatment of external or internal visceral injuries. Where the method of administration allows for cell migration (e.g., intravenous administration), the mesenchymal cells will migrate in vivo to the site of the wound where they can enhance wound healing. Genetically engineered mesenchymal cells may be used in this fashion to deliver gene products to the site of the wound; e.g., genes for Factor VIII, growth factors, etc. may be useful in this regard. Alternatively, methods of administration which do not allow for migration may allow the mesenchymal cells, genetically engineered or otherwise, to take up residence at the site of administration where they can deliver gene products to the local environment, and/or systemically.

On the other hand, protocols may be designed to inhibit or remove these cells in vivo such as by the administration of monoclonal antibodies to specific surface markers, in the treatment of chronic diseases with noted fibrosis, particularly conditions of excessive fibroses such as myelofibroses, histiocytoses, hepatic cirrhosis, keloid formation, scleroderma, etc. In addition, the inhibition of migration of these cells into wound sites may prevent excessive scar formation.

The blood-borne mesenchymal cells may be quantified in peripheral blood samples obtained from individuals. Abnormally low or high concentrations of such cells (as compared to values determined for healthy individuals) may be correlated with diseases or disorders. The quantification of the blood-borne mesenchymal cells may be accomplished by morphological analysis, biological activities, or preferably by immunochemical means. For example, antibodies specific for vimentin, fibronectin, collagen I, or collagen III may be used individually or in combination for the detection and quantification of these cells.

5.5. IDENTIFICATION OF NEW MARKERS AND NOVEL CYTOKINES IN THE BLOOD BORNE MESENCHYMAL CELLS

Also within the scope of the invention is the production of polyclonal and monoclonal antibodies which recognize novel antigenic markers expressed by the blood-borne mesenchymal cells. Such antibodies may have a variety of uses such as the isolation and characterization of blood-borne mesenchymal cells by affinity chromatography. Various procedures known in the art may be used for the production of antibodies to these mesenchymal cells. Various host animals can be immunized by injection with viable isolated mesenchymal cells, fixed cells or membrane preparations, including but not limited to rabbits, hamsters, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Monoclonal antibodies to novel antigens on these mesenchymal cells may be prepared by using any technique which provides for the production of antibody molecules by continuous cell lines in culture. These include, but are not limited to, the hybridoma technique originally described by Kohler and Milstein (1975, Nature 256, 495–497), and the more recent human B-cell hybridoma technique (Kosbor et al., 1983, Immunology Today 4:72; Cote et al., 1983, Proc. Natl. Acad. Sci. 80:2026–2030) and the EBV-hybridoma technique (Cole et al., 1985, Monoclonal Antibodies and Cancer Therapy, Alan R. Liss, Inc., pp. 77–96). Techniques developed for the production of "chimeric antibodies" by splicing the genes from a mouse antibody molecule of appropriate antigen specificity together with genes from a human antibody molecule can be used (e.g., Morrison et al., 1984, Proc. Natl. Acad. Sci., 81:6851–6855; Neuberger et al., 1984, Nature, 312:604–608; Takeda et al., 1985, Nature 314:452–454). In addition, techniques described for the production of single chain antibodies (U.S. Pat. No. 4,946,778) can be adapted to produce single chain antibodies.

Syngeneic, allogeneic, and xenogeneic hosts may be used for injection of blood-borne mesenchymal cells prepared in viable form, or in fixed form, or as extracted membrane preparations thereof. Monoclonal antibodies can be screened differentially by selective binding to mesenchymal cells, but not to other blood cells.

Antibody fragments which contain the binding site of the molecule may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments.

The ability of blood-borne mesenchymal cells to migrate into wound sites indicates that they participate in the wound healing response naturally. These cells may function through the release of cytokines and/or membrane-bound accessory molecules involved in cell-cell contact. Therefore, mesenchymal cells may be used as a source for identifying novel cytokines and cell surface accessory molecules and the genes encoding therefor.

In order to identify new cytokines that may be produced by the mesenchymal cells, long-term mesenchymal cell cultures may be established or continuous cell lines may be generated by transforming the cells to tumor cells using a virus or a chemical. Culture supernatants may be directly analyzed by applying them to various cell types or in various animal models, which can then be assayed for the appropriate desired biological response. The cells may be metabolically labelled and their supernatants subjected to biochemical analysis to identify candidate proteins responsible for the observed bioactivity. Additionally, cytokines may be identified by inducing cytokine production in the cells. To this end, the cells may be exposed or contacted with an agent that induces the expression and production of a cytokine. A number of agents known to induce cytokine production in other cells may be useful in this approach. Such agents may include but are not limited to calcium ionophores, endotoxins, phorbol esters, known cytokines, chemokines, growth factors, hormones and/or other mediators. Having identified a candidate protein by SDS-PAGE and/or by biologic activity, the protein may be purified by a variety of techniques known in the art including but not limited to SDS-preparative gels, ion exchange chromatography, isoelectric focusing gels and other types of chromatography. Purity of the proteins can be verified by SDS-PAGE, quantified by protein assays, their activities confirmed in bioassays, and used as immunogens for the production of polyclonal and monoclonal antibodies.

The purified proteins can be further tested in bioassays to stimulate and/or inhibit proliferation and/or differentiation of a variety of indicator cell lines of diverse tissue types. Radiolabelled proteins may also be used to identify their cell surface receptors by methods such as affinity labelling. Specific antibodies to the cytokines may be used to identify and quantify membrane forms and secreted forms of the cytokines, to study their biosynthetic pathways, to affinity purify the proteins and to immunoscreen expression libraries for the molecular cloning of the coding sequences.

6. EXAMPLE: IDENTIFICATION, ISOLATION AND CHARACTERIZATION OF THE BLOOD-BORNE MESENCHYMAL CELLS

6.1. MATERIALS AND METHODS

6.1.1. CELL ISOLATION FROM BLOOD AND CULTURING

Blood-borne mesenchymal cells were isolated from whole blood, for instance human or mouse blood. For human cells, 60 ml of blood was drawn by venipuncture into a heparinized syringe and diluted 1:1 with phosphate-buffered saline (PBS). Diluted blood then was layered on Ficoll-Hypaque density medium and centrifuged at room temperature for 30 minutes at 450×g. Leukocytes that formed a band above the red blood cells were obtained and washed with PBS by centrifuging three additional times. Pelleted cells were resuspended in 25 ml Dulbecco's Modified Eagle's Medium/20% fetal bovine serum (FBS)/and 0.1% gentamicin. The cells then were plated onto a 150 mm tissue culture plate. After 24 hours, medium together with non-adherent cells was aspirated and replaced with fresh medium. Medium was replaced with fresh medium weekly and adherent cells enumerated at intervals.

6.1.2. IMMUNOFLUORESCENCE AND CYTOFLUOROGRAPHY

In some cases, cells were seeded into wells that had microscope slide coverslips resting on the bottom of the wells. Spot immunofluorescence was then performed on cells cultured for 4 weeks on 13 mm glass coverslips. For analysis, the slips were removed from the plates, washed twice with PBS, and fixed by immersion in 3.5% formaldehyde for 20 minutes. The cells were washed once with PBS, then immersed for 7 minutes at −20° C. in 70% ethanol. The 70% ethanol was replaced with 100% ethanol in which the cells were immersed for an additional 7 minutes at −20° C. The cells then were immersed in 70% ethanol for 5 minutes at −20° C. and washed 3× with PBS.

Fifty microliters of a primary antibody, diluted 1:10 in 3% bovine serum albumin (BSA) in PBS, added to the fixed cells and incubated for 30 minutes at room temperature. The cells were washed twice with PBS before 50 µl of a fluorochrome-conjugated secondary antibody, diluted 1:10 in 3% BSA in PBS, was added for another 30 minutes at room temperature. For double staining with two antibodies, cells were incubated as above with two directly conjugated antibodies of different fluorescence signals (i.e., FITC and rhodamine or Texas Red). The cells were washed twice with PBS, preserved with 80% glycerol/50 mM N-propyl gallate and analyzed by fluorescence microscopy.

Cytofluorography was performed on 4 week cultured cells. Adherent cells were removed by gentle scraping and elutriation. After washing 3 times in PBS and enumeration, the cells were resuspended in 1% BSA in PBS at a concentration of 5×10$^6$ cells/ml. 3×10$^5$ cells were aliquoted into polystyrene tubes (10×75 mm) and 10 µl of undiluted primary antibody added for 45 minutes on ice in the dark, then washed 3× in 1% BSA/PBS. Ten µl of a second antibody-fluorescent dye conjugate was added (if the primary antibody was not directly conjugated to a fluorescent dye) and the cells were incubated for 40 minutes on ice in the dark. For double staining, cells were incubated as above with two directly conjugated antibodies of different fluorescence properties (i.e., FITC and rhodamine or Texas Red). The cells were washed 3× in 1% BSA/PBS, resuspended in 25 µl 1% BSA/PBS and 100 µl 3.5% formaldehyde, and stored at 4° C. in the dark until ready for cytofluorography. Cells were analyzed with a Becton Dickinson FACS 440 and the PROFILE 2 by Coulter.

6.1.3. CELL SORTING

Fluorescence-activated cell sorting was performed to purify to homogeneity the spindle-shaped mesenchymal cell type in the blood-derived cultures. These studies utilized a Becton Dickinson FACs 440 to isolate the mesenchymal cells either by cell size (light scatter) or by specific cell surface marker expression, as determined by specific reactivity with antibodies.

By Size:

Four week cultures were scraped, counted, and washed three times in PBS. The cells were resuspended at a concentration of $5 \times 10^5$/ml in PBS and kept on ice until ready to be sorted. For culturing after sorting, the entire procedure was carried out under sterile conditions, the cells were collected into DMEM/20% FBS/0.1% gentamicin and plated.

By Cell Surface Markers:

Four week cultures were scraped, counted, and washed three times in PBS. The cells were resuspended at a concentration of $5 \times 10^5$/ml in 1% BSA/PBS. $3 \times 10^5$ cells were aliquoted into small polystyrene tubes and reacted with 10 $\mu$l of undiluted primary antibody. The cells were incubated on ice for 45 minutes in the dark and then washed three times in 1% BSA/PBS. Ten microliters of a fluorescent dye-conjugated antibody was added (if the primary was not directly conjugated) and the cells were incubated for 40 minutes on ice in the dark. If the cells were to be double stained, they were incubated as above, substituting directly-conjugated antibodies of different fluorescence colors (i.e., FITC and rhodamine or Texas Red). The cells were washed three times in 1% BSA/PBS, resuspended at a concentration of $5 \times 10^5$/ml in 25 $\mu$l 1% BSA/PBS and 100 $\mu$l 3.5% formaldehyde, and stored at 4° C. in the dark until ready for sorting. If the cells were to be cultured after the sort, they were collected into DMEM/20% FBS/0.1% gentamicin and plated.

6.1.4. REAGENTS

The majority of the antibodies used in the studies described herein were purchased from Becton Dickinson (San Jose, Calif.). The exceptions are: anti-fibronectin, anti-desmin, anti-smooth muscle $\alpha$-actin and anti-laminin, (Sigma, St. Louis, Mo.), anti-vimentin (Labsystems, Raleigh, N.C.), anti-collagen (Chemicon, Temecula, Calif.) and anti-von Willebrands factor (Accurate).

6.1.5. PROLIFERATION ASSAY

To measure the growth of the fibroblasts in response to GM-CSF, cells were cultured in 6-well plates such that each well contained white cells from 5 ml of whole blood. After two weeks in culture, the cells were subjected to one of four conditions: no GM-CSF (control), 25U GM-CSF, 50U GM-CSF or 100U GM-CSF per ml. The media and GM-CSF were replaced weekly. The cells were counted by marking off a set field on the plate and that area was manually counted each week. The percentage of fibroblasts per field reflected the number of cells that had the classical fibroblast morphology as compared to the total number of cells in the area being examined.

6.1.6. MIGRATION ASSAY

Wound chambers were implanted into subcutaneous pockets in the flanks of mice. The wound chambers consisted of a perforated 3 cm length of SILASTIC tubing (Dow Corning) that contained a piece of polyvinyl alcohol sponge (Unipoint, N.C.) that had been sterilized by autoclaving. Incisions were closed with wound clips and the mice were monitored for infection. Once weekly post implantation, the wound fluid was percutaneously aspirated using a 1 cc syringe with a 25 g needle. The cells obtained were cultured in DMEM/20% FBS/0.1% gentamicin. Cells were analyzed by morphology and fluorescence staining techniques for fibroblast-specific markers.

6.2. RESULTS

Over a period of 2–4 weeks in culture, a gradual depletion of non-dividing and loosely adherent cells occurred. At the same time, isolated clusters of adherent, dividing cells were readily identified. In short-term cultures, these cultured cells fell into one of two distinct morphological profiles, a "round" cell type, and a "spindle-shaped" fibroblast-like cell type. Cytofluorography analysis performed on these cells indicated that they consisted of two subpopulations. By light scattering analysis, the round cells appeared as "small" cells, while the spindle-shaped cells appear as "large" cells. In short-term cultures (e.g., 1–2 weeks), the round cell population was a mixture of lymphocytes and cells that displayed the fibroblast-like phenotype. In long-term cultures, the vast majority of all the surviving cells had the mesenchymal cell phenotype.

Immunofluorescence analysis for selected cell surface markers then was performed by direct visualization under fluorescence microscopy (spot immunofluorescence) and by cytofluorography. The two distinct cell types were further separated, purified and characterized by fluorescence-activated cell sorting (FACs).

The large "spindle-shaped" cell was identified by antibody staining to be a mesenchymal cell type that displayed typical fibroblast markers; i.e., collagen I, III, vimentin, and fibronectin. These results are summarized in Table 1. Cell-sorting by size or immunofluorescence, followed by specific staining, confirmed the cell type described above and the phenotypic analysis shown in Table 1. Further, these cells were shown to be larger and more granular than peripheral blood leukocytes (FIG. 1A and FIG. 1B).

TABLE I

Summary Of Cell Surface Phenotype Of
Large Spindle-Shaped Mesenchymal Cells
Derived from the Peripheral Blood

| POSITIVE EXPRESSION FOR: | NEGATIVE EXPRESSION FOR: |
|---|---|
| MHC class II | T cell receptor ($\alpha\beta$ and $\gamma\delta$) |
| CD11b | CD3 |
| CD11c | CD4 |
| CD13 | CD8 |
| CD34 | CD11a |
| CD45 | CD14 |
| Vimentin | CD16 |
| Fibronectin | CD19 |
| Collagen I | CD25 |
| Collagen III | CD33 |
|  | CD38 |
|  | CD44 |
|  | CD54 |
|  | CD56 |
|  | Cytokeratin |
|  | Von Willebrand's factor |
|  | Desmin |
|  | smooth muscle cell $\alpha$-actin |
|  | Laminin |

Blood-borne mesenchymal cells could be expanded in vitro by addition of granulocyte-macrophage colony stimulating factor (GM-CSF) at a concentration of 50 U/ml (FIG. 2).

Mice were experimentally implanted with wound chambers in their back. The migration of a blood-borne murine cell population corresponding morphologically to the human blood-borne mesenchymal cells into the chambers was observed.

The present invention is not to be limited in scope by the exemplified embodiments which are intended as illustrations of single aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for enhancing wound healing comprising administering isolated mammalian blood-resident cells that display surface phenotypic markers of fibroblasts and phenotypic markers of hematopoietic stem cells, in which the phenotypic markers of hematopoietic stem cells are CD45 and CD34, to a mammalian recipient suffering from a wound, wherein the isolated mammalian blood-resident cells are from the same mammalian species as the mammalian recipient.

2. The method of claim 1 in which the cells are administered intravenously.

3. The method of claim 1 in which the cells are administered topically.

4. The method of claim 1 in which the recipient is a human.

5. A method of enhancing wound healing of a wound in a mammal comprising populating the wound with isolated mammalian blood-resident cells that display surface phenotypic markers of fibroblasts and phenotypic markers of hematopoietic stem cells, in which the phenotypic markers of hematopoietic stem cells are CD45 and CD34, , wherein the isolated mammalian blood-resident cells are from the same mammalian species as the wounded mammal.

6. The method of claim 5 in which the cells are administered intravenously.

7. The method of claim 5 in which the cells are administered topically.

8. The method of claim 5 in which the recipient is a human.

\* \* \* \* \*